US007621922B2

(12) United States Patent
Schendel et al.

(10) Patent No.: US 7,621,922 B2
(45) Date of Patent: Nov. 24, 2009

(54) FACIAL OSTEODISTRACTION DEVICE

(75) Inventors: Stephen A. Schendel, Palo Alto, CA (US); Shaher A. Ahmad, Plano, TX (US); Lisa Regina Thornhill, Dallas, TX (US); Viorel Mocanu, Lewisville, TX (US)

(73) Assignee: OsteoMed L.P., Addison, TX (US)

( * ) Notice: Subject to any disclaimer, the term of this patent is extended or adjusted under 35 U.S.C. 154(b) by 823 days.

(21) Appl. No.: 10/924,315

(22) Filed: Aug. 23, 2004

(65) Prior Publication Data
US 2005/0021045 A1 Jan. 27, 2005

Related U.S. Application Data

(63) Continuation-in-part of application No. 10/440,001, filed on May 16, 2003, which is a continuation of application No. 09/988,529, filed on Nov. 20, 2001, now Pat. No. 6,589,250.

(51) Int. Cl.
*A61B 17/58* (2006.01)
*A61B 17/60* (2006.01)
(52) U.S. Cl. .......................... 606/105; 433/7
(58) Field of Classification Search ............ 606/53–57, 606/60, 70, 71, 105, 59, 90; 433/7, 24, 17, 433/18
See application file for complete search history.

(56) References Cited

U.S. PATENT DOCUMENTS

| | | | |
|---|---|---|---|
| 1,504,942 A | 8/1924 | Comegys | |
| 2,362,741 A | 2/1944 | Berke | 128/83 |
| 4,157,715 A | 6/1979 | Westerhoff | 606/60 |
| 4,167,061 A | 9/1979 | Forster | 433/5 |
| 4,468,196 A * | 8/1984 | Keller | 433/24 |
| 4,676,745 A | 6/1987 | Zurita | 433/6 |
| 4,713,000 A * | 12/1987 | Rosenberg | 433/18 |
| 5,147,358 A | 9/1992 | Remmler | 606/57 |
| 5,376,091 A | 12/1994 | Hotchkiss et al. | 606/55 |
| 5,466,261 A | 11/1995 | Richelsoph | 623/23.47 |
| 5,700,263 A | 12/1997 | Schendel | 606/57 |
| 5,807,382 A | 9/1998 | Chin | 606/53 |
| 5,846,245 A | 12/1998 | McCarthy et al. | 606/105 |
| 5,885,283 A * | 3/1999 | Gittleman | 606/57 |
| 5,885,289 A | 3/1999 | Muller | 606/71 |
| 5,885,290 A | 3/1999 | Guerrero | 606/71 |
| 5,902,304 A | 5/1999 | Walker et al. | 606/71 |

(Continued)

OTHER PUBLICATIONS

Pending U.S. Appl. No. 10/440,001, entitled "Maxillary Distraction Device," filed May 16, 2003, 17 pages (Specification, Claims, Abstract, and Drawings), May 16, 2003.

(Continued)

*Primary Examiner*—Pedro Philogene
(74) *Attorney, Agent, or Firm*—Baker Botts L.L.P.

(57) ABSTRACT

A system for midface distraction including a left side distraction mechanism and a right side distraction mechanism, each including: an implantable anchor configured to be coupled to a bone of the malar region, an implantable anchor configured to be coupled to a bone of the cranium, and a distraction rod coupling the anchors. The system also includes a maxillary bridge configured to couple the left side distraction mechanism with the right side distraction mechanism and wherein couplings between the maxillary bridge and the right and left distraction mechanisms are configured to be internal to a patient.

17 Claims, 6 Drawing Sheets

U.S. PATENT DOCUMENTS

| | | | |
|---|---|---|---|
| 6,001,097 A | 12/1999 | Campopiano | 606/57 |
| 6,123,707 A | 9/2000 | Wagner | 606/61 |
| 6,129,728 A | 10/2000 | Schumacher | 606/71 |
| 6,139,316 A | 10/2000 | Sachdeva | 433/7 |
| 6,187,004 B1 | 2/2001 | Fearon | 606/57 |
| 6,267,589 B1 | 7/2001 | Farzin-Nia et al. | 433/7 |
| 6,322,566 B1 * | 11/2001 | Minoretti et al. | 606/105 |
| 6,358,255 B1 * | 3/2002 | Testa | 606/105 |
| D460,184 S | 7/2002 | Schendel et al. | D24/133 |
| 6,423,069 B1 | 7/2002 | Sellers | 606/71 |
| 6,589,250 B2 | 7/2003 | Schendel | 606/105 |
| 6,908,469 B2 * | 6/2005 | Sellers et al. | 606/105 |

OTHER PUBLICATIONS

PCT, International Search Report and Written Opinion (ISA/US) for PCT/US2005/18057, 7 pages, Aug. 24, 2006.

* cited by examiner

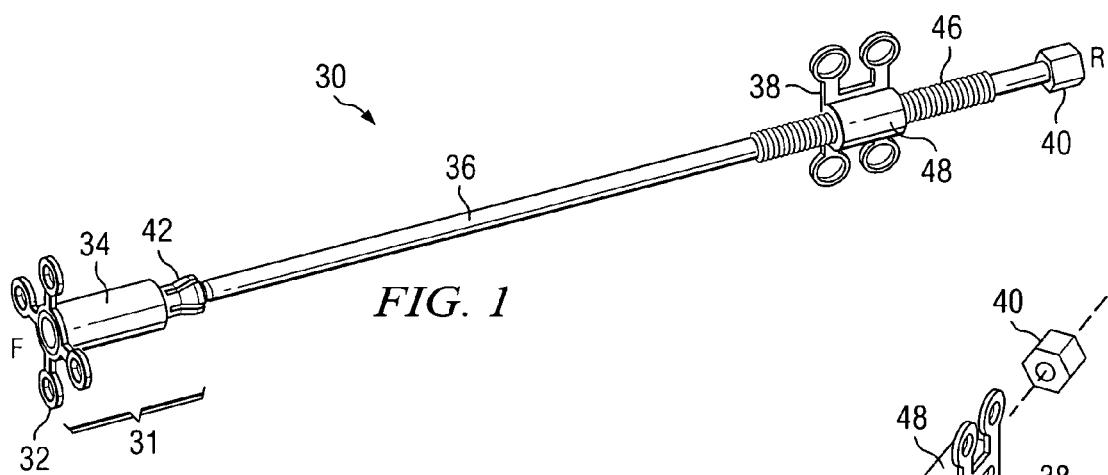
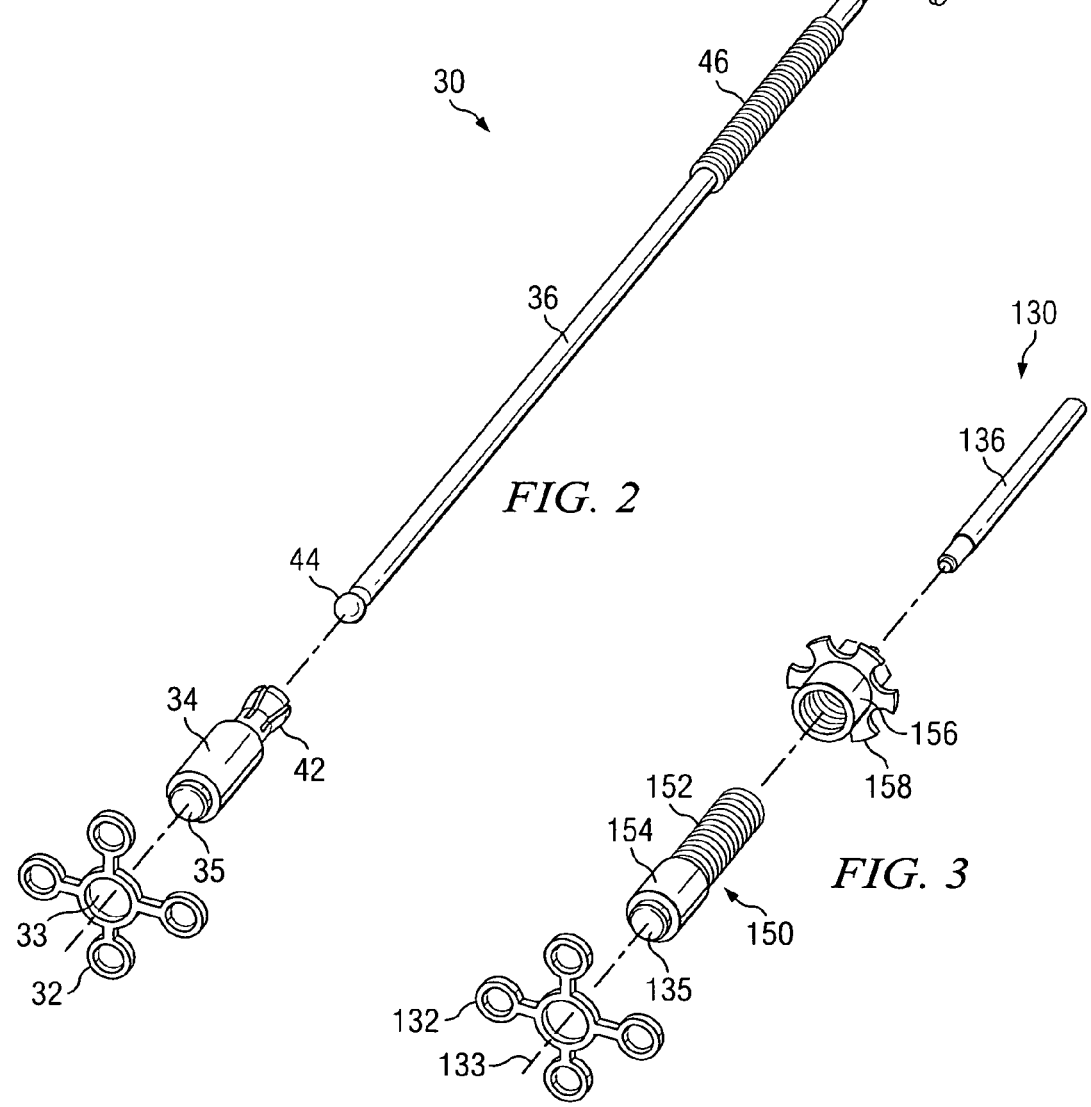

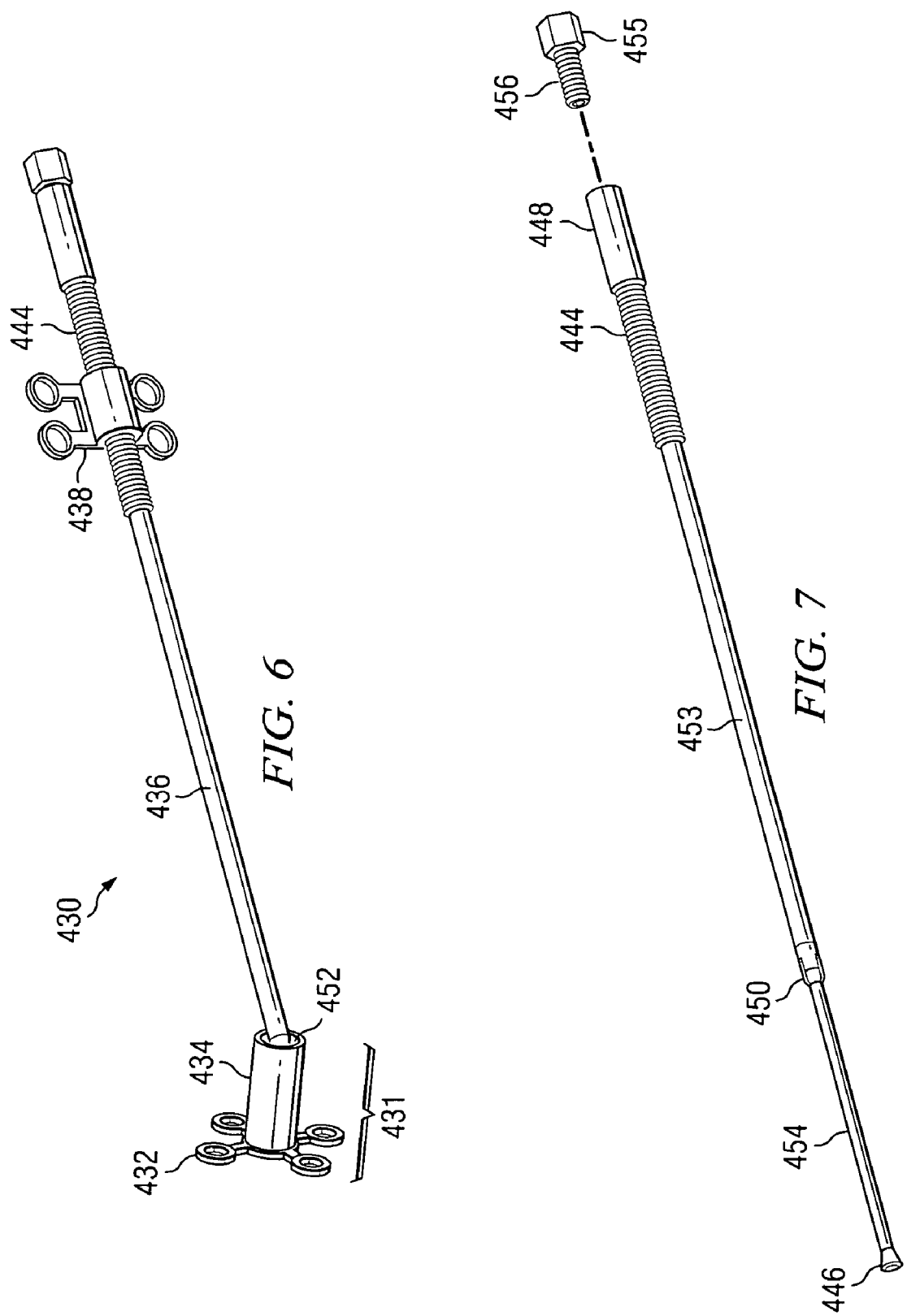

FACIAL OSTEODISTRACTION DEVICE

CROSS REFERENCE TO RELATED APPLICATIONS

This application is a continuation-in-part of U.S. patent application Ser. No. 10/440,001 filed by Stephen A. Schendel on May 16, 2003, which is a continuation of U.S. patent application Ser. No. 09/988,529 filed by Stephen A. Schendel on Nov. 20, 2001, now U.S. Pat. No. 6,589,250.

TECHNICAL FIELD OF THE INVENTION

The present invention relates to a device for manipulation of facial bones, and more particularly, the invention relates to a device for distraction of the midface and maxilla.

BACKGROUND OF THE INVENTION

Bones sometimes develop at different rates, leaving some bones disproportionately shorter than other bones. Alternatively, injury may leave a bone shorter than its original length. Such a condition may lead to difficulties in a patient's movement. For instance, a patient with a shortened tibia may need special shoes for assistance in walking. A small jaw may cause difficulties in chewing or breathing (e.g., obstructive sleep apnea). Moreover, deformations are often psychologically distressing to the patient, especially when the deformations occur in craniofacial bones.

One procedure for lengthening bones is referred to as osteodistraction. According to an osteodistraction procedure, an abnormally short bone is cut into two segments. The two segments are secured to a brace that permits the segments to be drawn apart. New bone then grows in the space between the separated bone segments, and eventually couples the two segments together into a lengthened bone. When the separated bone segments have been fully fused in this manner, the brace may be removed.

SUMMARY OF THE INVENTION

In accordance with teachings of the present invention, the disadvantages and problems associated with osteodistraction of the midface and maxilla have been substantially reduced or eliminated. In particular, the system and method described herein provide for large advancements of the midface, while providing stability across the midline.

In accordance with one embodiment of the present invention, a system for midface distraction includes left and right side distraction mechanisms, which each include an implantable anchor configured to be coupled to a bone of the malar region, an implantable anchor configured to be coupled to a bone of the cranium, and a distraction rod coupling the anchors. The system also includes a maxillary bridge configured to couple the left side distraction mechanism with the right side distraction mechanism, and wherein couplings between the maxillary bridge and the right and left distraction mechanisms are configured to be internal to a patient.

The system may also include the distraction rods having external threads operable to engage internally threaded housings on the cranial anchors. The distraction rods may also be coupled to the malar anchors by ball-and-socket joints. The system may further include at least a third anchor operable to couple the maxillary bridge to the maxilla bone. The maxillary bridge may be coupled to the right side distraction mechanism by a right side distraction arm and the maxillary bridge may be coupled to the left side distraction mechanism by a left side distraction arm, wherein the right and left side distraction arms each include a substantially horizontal distraction screw configured to move the maxillary bridge substantially horizontally in relation to the right and left side distraction mechanisms, and a substantially vertical distraction screw configured to move the maxillary bridge substantially vertically in relation to the right and left side distraction mechanisms. The maxillary bridge may also include a plurality of connection points operable to couple the maxillary bridge to an upper dentition.

In accordance with another embodiment of the present invention, a system for midface distraction includes a distraction rod and an implantable anchor configured to be coupled to a bone of the malar region and a first end of the distraction rod. The system also includes a second implantable anchor configured to be coupled to a bone of the cranium and a second end of the distraction rod. The first end of the distraction rod being configured such that the first implantable anchor and the distraction rod may be coupled and allow for a free range of motion for the second end of the distraction rod.

Technical advantages of certain embodiments of the present invention include providing advancement of the midface, while enhancing stability across the midline of the face. Removal procedures are also simplified, which reduces patient trauma and scarring. Patient trauma and scarring are further reduced by obviating the need for connections through the skin of the patient's face. Further, a patient's quality of life during the distraction period may be improved as the device is internal to the patient, making the device less noticeable and less likely to encumber daily activities.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present invention and its advantages, reference is now made to the following descriptions, taken in conjunction with the accompanying drawings, in which:

FIG. 1 is an isometric view of a midface distraction device, in accordance with a particular embodiment of the present invention;

FIG. 2 illustrates an expanded view of the midface distraction device of FIG. 1, in accordance with a particular embodiment of the present invention;

FIG. 3 illustrates an expanded view of a midface distraction device in accordance with a particular embodiment of the present invention;

FIG. 6 is an isometric view of a midface distraction device, in accordance with a further alternative embodiment of the present invention;

FIG. 7 illustrates an expanded view of the midface distraction device of FIG. 6, in accordance with a particular embodiment of the present invention;

DETAILED DESCRIPTION OF THE INVENTION

Figure 4:
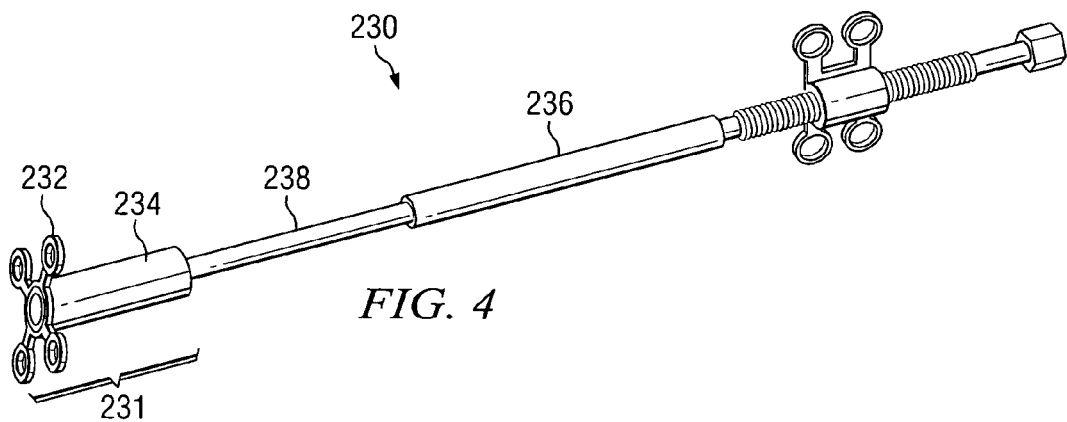
FIG. 4 is an isometric view of a midface distraction device, in accordance with an alternative embodiment of the present invention.

FIGS. 1 and 2 illustrate one embodiment of midface distraction device 30. Distraction devices such as midface distraction device 30 may be used to lengthen bones to correct congenital abnormalities and deformations following fractures or injuries. Osteodistraction is a procedure for lengthening bones by cutting a bone into two segments. The segments are drawn apart by a distraction device, such as midface distraction device 30. New bone grows in between the separated bone segments, eventually coupling the two segments together, resulting in a lengthened bone. As the bone grows in between the separated segments, the segments may be drawn apart further until the desired bone length is achieved. Once the desired bone length is achieved, the device may remain on the bone until the newly grown bone is sufficiently strong, and then be removed.

In a particular embodiment, midface distraction device 30 could be a Le Fort III distraction device. Le Fort III distraction devices may be used to lengthen the bones of the midface. A transverse cut is made through the bones of the midface at the desired distraction line. A distraction device may be implanted such that it may impart a separating force on the bones of the face behind the cut. The distraction device may be used to manipulate the bones to the desired position, or to a position that accommodates bone growth, and then be adjusted periodically as needed.

Throughout this description reference will be made to the front and rear of midface distraction device 30, the front and rear of various alternative embodiments, and the front and rear of components of midface distraction device 30 and the various alternative embodiments. The front is designated by the letter F in FIG. 1, and the rear is designated by the letter R in FIG. 1. When implanted in a patient, the front and rear designations correspond to the face and back of the head respectively.

FIG. 1 is an isometric view of midface distraction device 30, and FIG. 2 illustrates an expanded view of midface distraction device 30. As FIGS. 1 and 2 illustrate, midface distraction device 30 includes two anchors, malar anchor 32 and cranial anchor 38, adjustably coupled to a shaft, namely, distraction rod 36. Cranial anchor 38 is threadably coupled to distraction rod 36 such that distraction rod 36 may be moved forwards and rearwards in relation to cranial anchor 38. Malar anchor 32 is coupled to distraction rod 36 such that when distraction rod 36 is moved forward in relation to cranial anchor 38, malar anchor 32 also moves forward in relation to cranial anchor 38. In such a manner, distraction forces may be imparted to bones of the midface which are coupled to malar anchor 32.

Malar anchor 32 is configured to be mounted to a bone in the malar region. In the illustrated embodiment, malar anchor 32 is designed to be secured to the zygoma. Malar anchor 32 is also coupled to one end of malar spacer 34 to form anchor assembly 31. In the illustrated embodiment, Malar spacer 34 comprises a raised circular ridge 35 on its front end which is appropriately sized to mate with a corresponding hole 33 in the center of malar anchor 32. In an alternative embodiment malar spacer 34 may be mounted substantially flush against the rear side of malar anchor 32 without raised circular ridge 35. In a further alternative embodiment, malar spacer 34 could pass through an enlarged corresponding hole 33 in the malar anchor such that the front of malar spacer 34 is substantially flush with the front of malar anchor 32. In any of these described embodiments, malar spacer 34 and malar anchor 32 may then be secured by welding, or otherwise melding the two pieces. Anchor assembly 31 is then inserted through a drilled hole in the zygoma. Anchor assembly 31 is inserted from the front of the face such that malar anchor 32 is seated on the anterior surface of the zygoma and malar spacer 34 passes through the zygoma and protrudes from the posterior side of the zygoma. After insertion, anchor assembly 31 is secured in place by securing malar anchor 32 with bone screws, or other appropriate securing method, using connection loops 90.

In the illustrated embodiment, the rear end of malar spacer 34 includes a socket 42 that is adapted to receive one end of distraction rod 36. Distraction rod 36 has, at its front end, a spherical coupler, or ball 44. Ball 44 is sized to mate with socket 42. Ball 44 and socket 42 collectively form a ball-and-socket joint which pivotally secures distraction rod 36 to malar spacer 34. In this manner, the front end of distraction rod 36 is securely coupled to malar spacer 34, while the rear end remains free to be moved, to some degree, in nearly any direction, as a traditional ball-and-socket joint would allow. This free range of motion allows the rear end of distraction rod 36 to be moved up, toward the top of a patient's skull, or to be moved down, toward the patients jaw. Whether moved up or down, the rear end of distraction rod 36 is free to swing toward, or away from, the patient's skull so that contact with the patient's skull can be achieved regardless of the vertical orientation of distraction rod 36. In this manner distraction rod 36 may be mounted in a plurality of positions and still impart the proper distractive force on malar spacer 34 and malar anchor 32.

Distraction rod 36 also includes a threaded section 46. Threaded section 46 comprises external threads that engage internal threads of housing 48 on cranial anchor 38. The placement of threaded section 46 and the proportion of distraction rod 36 dedicated to threaded section 46 may vary depending on the desired placement of cranial anchor 38 and the amount of distraction desired. Generally, cranial anchor 38 would be coupled to the cranium in the area around the ear. Cranial anchor 38 may be coupled to the cranium by bone screws, or other suitable securing method, using connection loops 90. Securing cranial anchor 38 also serves to secure the rear end of distraction rod 36.

Hex nut 40 is coupled to approximately the rear end of distraction rod 36. Hex nut 40 may be coupled to distraction rod 36 by press fitting, by welding, or other suitable method. Hex nut 40 is configured to interface with tools, such as a wrench, which would facilitate rotation of hex nut 40 and thereby also rotate distraction rod 36. In alternative embodiments, hex nut 40 could be a screw head configured to interface with tools, such as a Phillips or flat head screw driver or Allen wrench. Further alternate embodiments could alter the shape of hex nut 40 to be, for example, square or octagonal. As distraction rod 36 is turned the threads of threaded section 46 engage the threads of housing 48 on cranial anchor 38 and move distraction rod 36 forward or reward in relation to cranial anchor 38. As distraction rod 36 is moved forward in relation to cranial anchor 38, ball 44 of distraction rod 36 rotates within socket 42. The forward motion of distraction rod 36 causes a corresponding forward motion of socket 42, malar spacer 34, malar anchor 32, and bones coupled to malar anchor 32. In such a manner, hex nut 40 may be rotated to increase the separation of the bone segments of the bone being distracted.

Once the desired bone length has been achieved and the bones have reached sufficient strength, hex nut 40 may be used to remove distraction rod 36. By rotating hex nut 40 in the opposite direction than that required for distraction, distraction rod 36 may be moved rearward in relation to cranial anchor 38. As distraction rod 36 is moved rearward in relation to cranial anchor 38 the force being exerted by the torque on hex nut 40 will overcome the coupling force of socket 42 and ball 44 causing a decoupling of socket 42 and ball 44. Once socket 42 and ball 44 are decoupled, threaded section 46 of distraction rod 36 may be disengaged from housing 48 on cranial anchor 38 and distraction rod 36 may be removed. Cranial anchor 38 may be removed along with distraction rod 36, it may be removed on its own after distraction rod 36 has been removed, or it may be left in the patient. Likewise, malar anchor 32 and malar spacer 34 may be removed or left in the patient. Leaving components of midface distraction device 30 in the patient may have the beneficial effects of reducing scarring and trauma while having few or no harmful effects on the patient.

FIG. 3 shows an alternative embodiment of a midface distraction device, which is labeled midface distraction device 130. Midface distraction device 130 does not utilize a ball-and-socket connection to couple distraction rod 136 and malar anchor 132. Instead, distraction rod 136 is coupled to malar anchor 132 by using a threaded spacer 150. Distraction rod 136 slides into a receiving hole in the rear of threaded spacer 150. This configuration allows distraction rod 136 to impart a distractive force forward into threaded spacer 150 and thereby into malar anchor 132. Malar anchor 132 is coupled to the forward side of threaded spacer 150 and washer 156 is then threaded onto threaded spacer 150.

Threaded spacer 150 comprises a threaded portion 152 and an unthreaded portion 154. Unthreaded portion 154 may be of a larger diameter than threaded portion 152. In the illustrated embodiment, threaded spacer 150 comprises a raised circular ridge 135 on its front end which is appropriately sized to mate with a corresponding hole 133 in the center of malar anchor 132. In an alternative embodiment, threaded spacer 150 may be mounted substantially flush against the rear side of malar anchor 132 without raised circular ridge 135. In a further alternative embodiment, threaded spacer 150 could pass through an enlarged corresponding hole 133 in the malar anchor such that the front of threaded spacer 150 is substantially flush with the front of malar anchor 132. In many of these described embodiments, threaded spacer 150 and malar anchor 132 may be secured by welding, or otherwise melding the two pieces. The combined assembly of malar anchor 132 and threaded spacer 150 is passed through a drilled hole in the zygoma such that threaded portion 152 of threaded spacer 150 at least partially protrudes from the posterior side of the zygoma, and malar anchor 132 sits substantially flush with the anterior side of the zygoma. A washer 156 is then coupled to threaded portion 152 of threaded spacer 150. Washer 156 is internally threaded to engage threaded portion 152 of threaded spacer 150. Washer 156 also includes a flange 158. Flange 158 abuts the posterior surface of the zygoma. Flange 158 provides added support for malar anchor 132 by further distributing the distractive forces imparted on the zygoma by midface distraction device 130.

FIG. 4 shows a further alternative embodiment of a midface distraction device, which is labeled midface distraction device 230. Midface distraction device 230 couples distraction rod 236 to the malar spacer 234 with a flexible rod 238. Flexible rod 238 serves to transmit the distractive forces from distraction rod 236 to anchor assembly 231 and thereby into the bone of the malar region being distracted. Flexible rod 238 accomplishes this force transmission while allowing selective placement of distraction rod 236 relative to anchor assembly 231.

Anchor assembly 231 comprises a malar anchor 232 and a malar spacer 234, which may be coupled in the same manner as the previously described embodiments. As in the previously described embodiments, anchor assembly 231 is coupled to a bone of the malar region by passing malar spacer 234 through a drilled hole in the bone of the malar region until malar anchor 232 abuts the surface of the bone. Malar anchor 232 is then coupled to the bone with bone screws or other appropriate coupling device.

Flexible rod 238 is then inserted into a receiving hole in the rear of anchor assembly 231. Flexible rod 238 can be coupled to anchor assembly 231 either before or after flexible rod 238 is coupled to distraction rod 236. Distraction rod 236 has a receiving hole at its front end which accepts the rear end of flexible rod 238. The coupling between distraction rod 236 and flexible rod 238 could be by press fitting, welding or otherwise melding the two pieces together, or it could be a friction fit allowing flexible rod 238 to rotate within the receiving hole of distraction rod 236. Either of the couplings of flexible rod 238 to anchor assembly 231 or flexible rod 238 to distraction rod 236 may be rotatable couplings. A rotatable coupling allows distraction rod 236 to be rotated and impart a distraction force on the flexible rod 238 and thereby on anchor assembly 231, while anchor assembly 231 remains fixed.

Flexible rod 238 may have the ability to deform elastically or inelastically while maintaining a constant axial length. The ends of flexible rod 238 may be bent to conform to skull curvatures. In any configuration, flexible rod 238 retains a constant length along its central axis, and may retain the ability to transmit a force along its central axis. In this manner, the front end of flexible rod 238 can be securely coupled to malar spacer 234, while the rear end, and thereby distraction rod 236, remains free to be moved, to some degree, in nearly any direction. This freedom of movement allows the rear end of distraction rod 236 to be moved up, toward the top of a patient's skull, or to be moved down, toward the patients jaw. Whether moved up or down, the rear end of distraction rod 236 is free to swing toward, or away from, the patient's skull so that contact with the patient's skull can be achieved regardless of the vertical orientation of distraction rod 236. In this manner distraction rod 236 may be mounted in a plurality of positions and still impart the proper distractive force on anchor assembly 231.

Flexible rod 238 may be made from a variety of materials and in one embodiment may comprise a nitinol wire.

Figure 5:
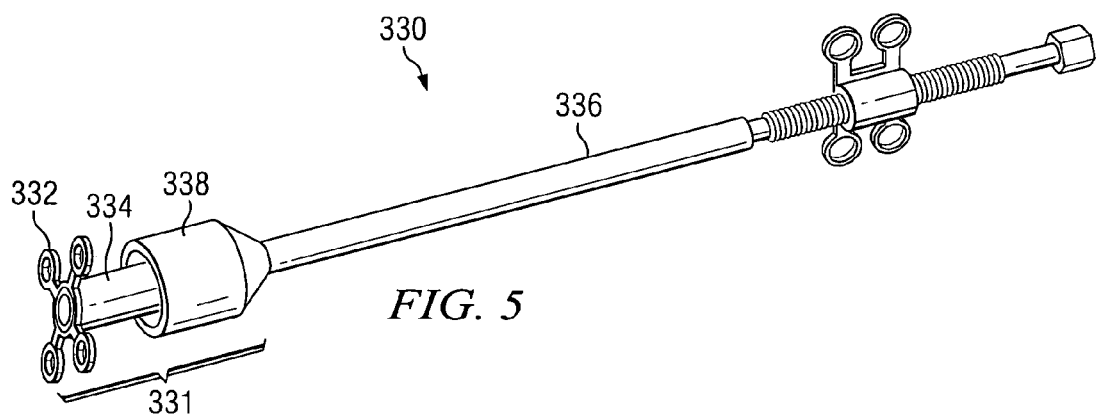
FIG. 5 is an isometric view of a midface distraction device, in accordance with a further alternative embodiment of the present invention.

FIG. 5 shows a further alternative embodiment of a midface distraction device, which is labeled midface distraction device 330. Midface distraction device 330 couples distraction rod 336 to the malar spacer 334 with a socket 338. Socket 338 serves to transmit the distractive forces from distraction rod 336 to anchor assembly 331 and thereby into the bone of the malar region being distracted. Socket 338 accomplishes this force transmission while allowing selective placement of distraction rod 336 relative to anchor assembly 331.

Anchor assembly 331 comprises a malar anchor 332 and a malar spacer 334, which may be coupled in the same manner as the previously described embodiments. As in the previously described embodiments, anchor assembly 331 is coupled to a bone of the malar region by passing malar spacer 334 through a drilled hole in the bone of the malar region until malar anchor 332 abuts the surface of the bone. Malar anchor 332 is then coupled to the bone with bone screws or other appropriate coupling device.

Socket 338 may be formed as part of distraction rod 336, or socket 338 may be coupled to the front end of distraction rod 336 after distraction rod 336 is formed. If distraction rod 336 and socket 338 are coupled after formation, the coupling could be by press fitting, welding or otherwise melding the two pieces together.

Socket 338 couples to the rear of anchor assembly 334 by a receiving hole in the forward side of socket 338. Malar spacer 334 contacts the rear wall of the receiving hole in the forward side of socket 338, and the two are held together by the distractive force imparted by distraction rod 336. In one embodiment, the receiving hole in the front of socket 338 is shaped to allow distraction rod 336 to pivot around malar spacer 334. In this manner, the front end of distraction rod 336 can be coupled to malar spacer 334, while the rear end remains free to be moved, to some degree, in nearly any direction. This freedom of movement allows the rear end of distraction rod 336 to be moved up, toward the top of a patient's skull, or to be moved down, toward the patients jaw. Whether moved up or down, the rear end of distraction rod 336 is free to swing toward, or away from, the patient's skull so that contact with the patient's skull can be achieved regardless of the vertical orientation of distraction rod 336. In this manner distraction rod 336 may be mounted in a plurality of positions and still impart the proper distractive force on anchor assembly 331.

FIG. 6 demonstrates a further alternative embodiment of a midface distraction device, which is labeled midface distraction device 430. FIG. 7 illustrates an expanded view of midface distraction device 430. As FIGS. 6 and 7 illustrate, midface distraction device 430 includes two anchors, malar anchor 432 and cranial anchor 438, adjustably coupled to a shaft, namely, distraction rod 436. Cranial anchor 438 is threadably coupled to distraction rod 436 such that distraction rod 436 may be moved forwards and rearwards in relation to cranial anchor 438. Malar anchor 432 is coupled to distraction rod 436 such that when distraction rod 436 is moved forward in relation to cranial anchor 438, malar anchor 432 also moves forward in relation to cranial anchor 438. In such a manner, distraction forces may be imparted to bones of the midface which are coupled to malar anchor 432.

Malar anchor 432 is configured to be mounted to a bone in the malar region. In the illustrated embodiment, malar anchor 432 is designed to be secured to the zygoma. Malar anchor 432 is also coupled to one end of malar spacer 434 to form anchor assembly 431. Malar spacer 434 and malar anchor 432 may then be secured by welding, or otherwise melding the two pieces. Anchor assembly 431 is then inserted through a drilled hole in the zygoma. Anchor assembly 431 is inserted from the front of the face such that malar anchor 432 is seated on the anterior surface of the zygoma and malar spacer 434 passes through the zygoma and protrudes from the posterior side of the zygoma. After insertion, anchor assembly 431 is secured in place by securing malar anchor 432 with bone screws, or other appropriate securing method.

In the illustrated embodiment, the rear end of malar spacer 434 includes a socket 452 that is adapted to receive one end of distraction rod 436. Distraction rod 436 is an assembly of three components. Hollow tube 453 forms the main body of distraction rod 436 and partially encloses the other two portions of distraction rod 436. Passing through the hollow center of hollow tube 453 is compression rod 454. The rear end of compression rod 454 couples to hex nut 455. The coupling between compression rod 454 and hex nut 455 may be by welding or other appropriate coupling method. Hex nut 455 includes an externally threaded section 456 which threads into the internally threaded rear end of hollow tube 453.

The rear end of compression rod 454 is passed through a hole in the front end of hollow tube 453. Compression rod 454 is fed into hollow tube 453 until a compression cone 446 on the front end of compression rod 454 abuts flared flanges 450 on the front end of hollow tube 453. Flared flanges 450 and compression cone 446 are appropriately sized such that compression cone 446 does not pass through flared flanges 450. Following insertion of compression rod 454 into hollow tube 453, hex nut 455 can be coupled to the rear end of compression rod 454 and threaded into the rear end of hollow tube 453.

Externally threaded section 456 of hex nut 455 threads into the rear end of hollow rod 453, but the remainder of hex nut 455 remains external to hollow tube 453. In this manner, the rear end of hex nut 455 remains accessible. Hex nut 455 is configured to interface with tools, such as a wrench, which would facilitate rotation of hex nut 455. In alternative embodiments, hex nut 455 could be a screw head configured to interface with tools, such as a Phillips or flat head screw driver or Allen wrench. Further alternate embodiments could alter the shape of hex nut 455 to be, for example, square or octagonal.

As hex nut 455 is rotated, the threads of externally threaded section 456 engage the internal threads on the rear end of hollow tube 453 and draw the two pieces apart. As hollow tube 453 and hex nut 455 are drawn apart, compression rod 454 and hollow tube 453 are draw together. Thus, as hollow tube 453 and hex nut 455 are drawn apart, compression cone 446 is drawn into flared flanges 450. As compression cone 446 is drawn into flared flanges 450, the flanges open radially to accept the increased diameter of compression cone 446. In this manner the front end of the assembled, but uncompressed, distraction rod 436 can be passed into the socket 452 of malar spacer 434. Hex nut 455 can be rotated to draw compression cone 446 into flared flanges 450. This causes flared flanges 450 to open and engage socket 452 in a manner that prevents withdrawal of distraction rod 436 from malar spacer 434. In one embodiment, a section of hollow tube 453, labeled end section 448, may be knurled to allow an installer to better grip hollow tube 453 and prevent it from rotating as hex nut 455 is rotated.

Flared flanges 450 and socket 452 are correspondingly designed to pivotally secure distraction rod 436 to malar spacer 434. In this manner, the front end of distraction rod 436 is securely coupled to malar spacer 434, while the rear end remains free to be moved, to some degree, in nearly any direction, as a traditional ball-and-socket joint would allow. This free range of motion allows the rear end of distraction rod 436 to be moved up, toward the top of a patient's skull, or to be moved down, toward the patients jaw. Whether moved up or down, the rear end of distraction rod 436 is free to swing toward, or away from, the patient's skull so that contact with the patient's skull can be achieved regardless of the vertical orientation of distraction rod 436. In this manner distraction rod 436 may be mounted in a plurality of positions and still impart the proper distractive force on malar spacer 434 and malar anchor 432.

Distraction rod 436 also includes a threaded section 444. Threaded section 444 comprises external threads that engage internal threads of cranial anchor 438. The placement of threaded section 444 and the proportion of distraction rod 436 dedicated to threaded section 444 may vary depending on the desired placement of cranial anchor 438 and the amount of distraction desired. Generally, cranial anchor 438 would be coupled to the cranium in the area around the ear. Cranial anchor 438 may be coupled to the cranium by bone screws, or other suitable securing method. Securing cranial anchor 438 also serves to secure the rear end of distraction rod 436.

Threaded section 444 and cranial anchor 438 are threaded in the opposite direction as externally threaded section 456 and the rear end of hollow tube 453. In one embodiment, for example, the threads of threaded section 444 and cranial anchor 438 may be right hand threads, while the threads on the rear end of hollow tube 453 and the externally threaded section 456 may be left hand threads. In this manner, when compression cone 446 is fully drawn into flared flanges 450 and distraction rod 436 is securely coupled to malar spacer 434, hex nut 455 may be used to rotate distraction rod 436. Distraction rod 436 may be rotated as one piece because hollow tube 453 is being securely held by compression cone 450 on the front end and hex nut 455 on the rear end. Further turning of hex nut 455 results in rotation of the entire assembled distraction rod 436.

As distraction rod 436 is turned the threads of threaded section 444 engage the threads of cranial anchor 438 and move distraction rod 436 forward in relation to cranial anchor 438. As distraction rod 436 is moved forward in relation to cranial anchor 438, the flared flanges 450 of distraction rod 436 rotate within socket 452. The forward motion of distraction rod 436 causes a corresponding forward motion of socket 452, malar spacer 434, malar anchor 432, and bones coupled to malar anchor 432. In such a manner, hex nut 455 may be rotated to increase the separation of the bone segments of the bone being distracted.

Once the desired bone length has been achieved and the bones have reached sufficient strength, hex nut 455 may be used to remove distraction rod 436. By rotating hex nut 455 in the opposite direction than that required for distraction, distraction rod 436 may be decoupled from malar spacer 434. This is achieved because as hex nut 455 is rotated the threads of externally threaded section 456 engage the threads on the end of hollow tube 453 and cause compression rod 454 to move forward in relation to hollow tube 453. This results in compression cone 446 moving forward relative to flared flanges 450. This allows flared flanges 450 to close and for distraction rod 436 to be withdrawn. Once socket 452 and distraction rod 436 are decoupled, threaded section 444 of distraction rod 436 may be disengaged from cranial anchor 438 and distraction rod 436 may be removed. Cranial anchor 438 may be removed along with distraction rod 436, it may be removed on its own after distraction rod 436 has been removed, or it may be left in the patient. Likewise, malar anchor 432 and malar spacer 434 may be removed or left in the patient. Leaving components of midface distraction device 430 in the patient has the beneficial effects of reducing scarring and trauma while having few or no harmful effects on the patient.

FIGS. 1-7 show different orientations of malar anchors 32, 132, 232, 332, and 432 to the respective malar spacers or threaded spacers 34, 134, 234, 334, and 434. As one of ordinary skill in the art would understand, the relative angle between malar anchors 32, 132, 232, 332, and 432 and their respective malar spacers or threaded spacers 34, 134, 234, 334, and 434 could be changed considerably and still fall within the scope of the present invention.

Figure 8:
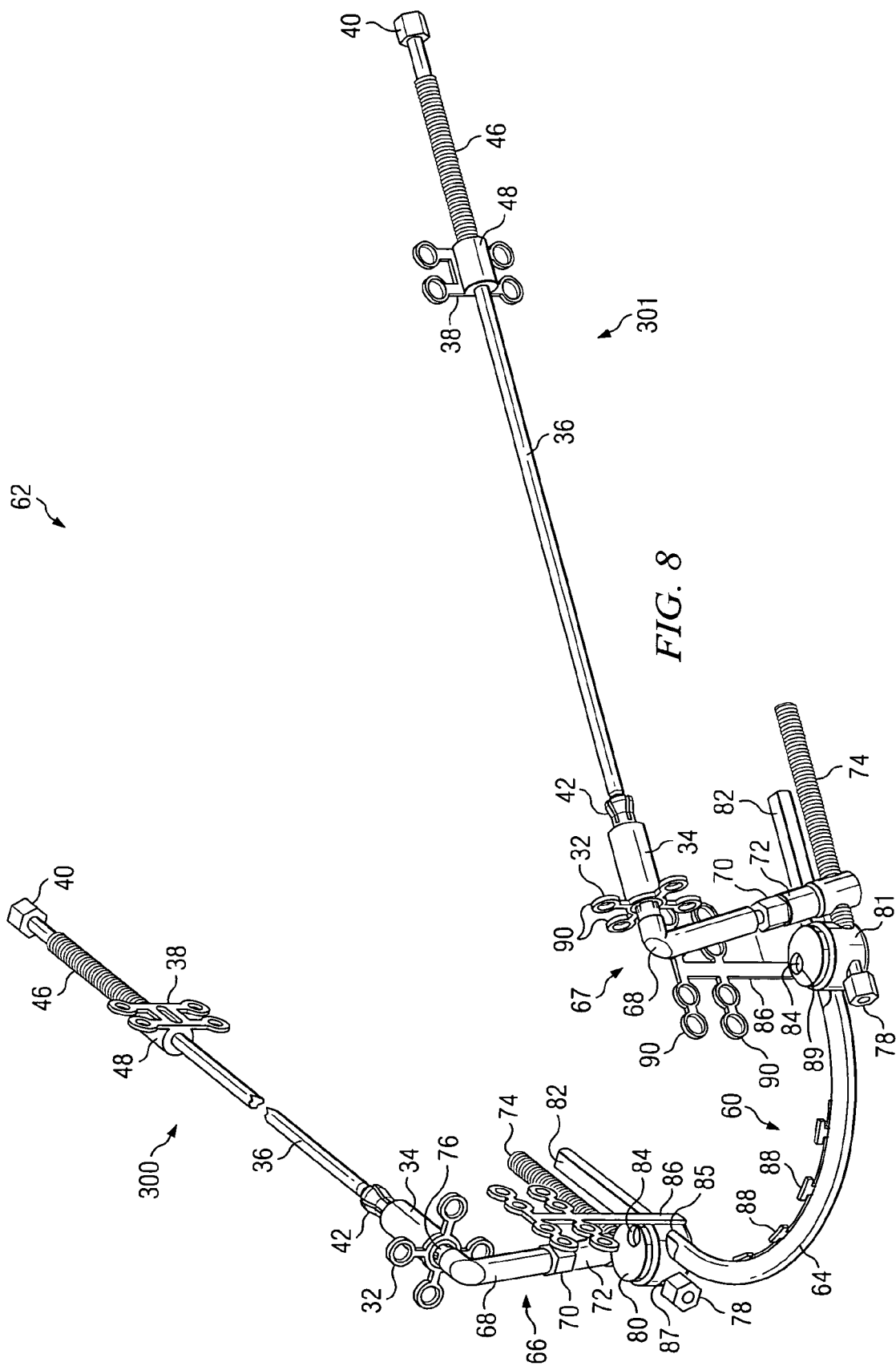
FIG. 8 is an isometric view of an implantable distraction unit, in accordance with a particular embodiment of the present invention.

FIG. 8 illustrates an implantable distraction unit 62 that includes a midface distraction device 300 configured to be coupled to the right side of a patient's skull, a midface distraction device 301 configured to be coupled to the left side of a patient's skull, and a maxillary spanner 60 coupling midface distraction devices 300 and 301. Midface distraction devices 300 and 301 may be one or more of midface distraction devices 30, 130, 230, 330, or 430 described above. Maxillary spanner 60 facilitates even distraction of the right and left sides of the face while also preventing buckling of the bones through the centerline of the face. Maxillary spanner 60 accomplishes this by holding midface distraction devices 300 and 301 a certain distance apart and thereby urging some of the distraction forces forward rather than inward.

In the illustrated embodiment, maxillary spanner 60 comprises a maxillary bridge 64 which couples a distraction arm 66 on the right side with a distraction arm 67 on the left side. Distraction arm 66 on the right side is further coupled to right side midface distraction device 300, and distraction arm 67 on the left side is further coupled to left side midface distraction device 301. Each distraction arm 66 and 67 includes an elbow 68 that serves to couple midface distraction device 300 or 301 to distraction arm 66 or 67, respectively. In the illustrated embodiment, this coupling occurs through a hole 33 in the front end of malar anchor 32. Expansion arms 76 on elbow 68 are snapped into a receiving hole in the front of malar spacer 34. In alternative embodiments a threaded coupling may be used in addition to, or in lieu of, the receiving hole of malar spacer 34.

Elbow 68 is coupled to vertical distraction arm 72 by vertical distraction nut 70. In one embodiment, vertical distraction nut 70 comprises external threads on both its top and bottom sides with the bottom threads being threaded in the opposite direction as the top threads. The top threads engage corresponding internal threads in the bottom of elbow 68. The bottom threads engage corresponding internal threads in the top of vertical distraction arm 72. When vertical distraction nut 70 is rotated, the top external threads of vertical distraction nut 70 engage the internal threads of elbow 68 causing vertical distraction nut 70 to move downwards in relation to elbow 68. Likewise, the bottom external threads of vertical distraction nut 70 engage the internal threads of vertical distraction arm 72 causing vertical distraction arm 72 to move downwards relative to vertical distraction nut 70. In an alternative embodiment, vertical distraction nut 70 comprises threads on only the top or bottom side. If the top of vertical distraction nut 70 comprises the external threads, then the bottom is rotatably coupled to vertical distraction arm 72. If the bottom of vertical distraction nut 70 comprises the external threads, then the top is rotatably coupled to elbow 68. This upward and/or downward movement defines one of the planes of distraction provided by distraction arms 66 and 67.

The other distraction plane of distraction arms 66 and 67 is defined by the movement of vertical distraction arm 72 relative to horizontal distraction screw 74. Vertical distraction arm 72 has an internally threaded hole which engages an externally threaded portion of horizontal distraction screw 74. Horizontal distraction screw 74 also comprises a hex nut 78. Hex nut 78 is coupled to approximately one end of horizontal distraction screw 74 by a press fit, by welding, or other appropriate method. Hex nut 78 is configured to interface with tools, such as a wrench, which would facilitate rotation of hex nut 78 and thereby also rotate horizontal distraction screw 74. In alternative embodiments, hex nut 78 could be a screw head configured to interface with tools, such as a Phillips or flat head screw driver or Allen wrench. Further alternate embodiments could alter the shape of hex nut 78 to be, for example, square or octagonal. When horizontal distraction screw 74 is rotated, the external threads of horizontal distraction screw 74 engage the internal threads of vertical distraction arm 72 and cause horizontal distraction screw 74 to move forward in relation to vertical distraction arm 72.

The two distraction planes of distraction arms 66 and 67 may be used to adjust maxillary spanner 60 to fit a particular patient. Additionally the distraction planes of distraction arms 66 and 67 may be utilized for maxillary distraction, either alone or at the same time that distraction of the midface is occurring.

In the illustrated embodiment, distraction arms 66 and 67 are coupled to maxillary bridge 64 by bridge couplers 80 and 81 respectively. Bridge coupler 80 will be described in detail and it should be understood that bridge coupler 81 is a mirror image, along the centerline of the face, of bridge coupler 80. Bridge coupler 80 has two substantially parallel holes, 85 and 87, drilled through it. Through hole 87 the unthreaded portion of horizontal distraction screw 74 passes. Through hole 85, bridge slide 82 of maxillary bridge 64 passes. Approximately perpendicular to hole 85 through which bridge slide 82 passes, there is also an internally threaded hole 89 which intersects the hole through which bridge slide 82 passes such that a set screw 84 may be utilized to maintain the relative spacing of bridge coupler 80 to maxillary bridge 64. When set screw 84 is threaded into its corresponding hole, set screw 84 contacts a substantially flat upper surface of bridge slide 82.

In one embodiment, at least the upper surface of bridge slide 82 is knurled, and set screw 84 engages the knurled surface. The length of bridge slide 82 is sufficient to allow adjustability of the relative spacing of bridge coupler 80 and maxillary bridge 64 such that maxillary spanner 60 may be adjusted to fit a variety of patients.

In the illustrated embodiment, bridge coupler 80 includes a maxillary anchor 86. Maxillary anchor 86 may be secured to the maxilla by bone screws or other appropriate securing medium. When secured to the maxilla, maxillary anchor 86 provides additional support for maxillary spanner 60 and implantable distraction unit 62. Maxillary anchor 86 also facilitates maxillary distraction either in conjunction with, or apart from, midface distraction. Alternative embodiments may not include maxillary anchor 86.

Maxillary spanner 60 may be used independently of midface distraction devices 300 and 301 when only maxillary distraction is desired. Malar anchors 32 can be coupled with socket 34, threaded spacer 150, or a specially designed receiver, and the assembly can be implanted as discussed above. Maxillary spanner 60 could then be coupled to these anchors without any other parts of distraction devices 300 or 301 being present. The maxilla bone could be cut at the desired distraction point and vertical distraction nut 70 and hex nut 78 may be used to adjust the vertical and horizontal distraction planes, respectively, of maxillary spanner 60. In this manner maxillary spanner 60 may be used for maxillary distraction when distraction of the midface is not desired.

In an alternative embodiment, midface distraction devices 300 and 301 could be used in conjunction with other maxillary distractors such as, for example, the maxillary distractor which is the subject of U.S. Pat. No. 6,589,250.

The illustrated embodiment also includes four coupling points 88. Coupling points 88 are used to couple maxillary bridge 64 to the upper dentition. This coupling may be accomplished by wiring coupling points 88 to the teeth of the upper dentition. One skilled in the art would realize that coupling points 88 could take a variety of forms, such as hooks or eyelets, while still performing their intended function. Alternative embodiments may include more than four coupling points 88 or may not include any coupling points 88.

The embodiments of the present invention illustrated in FIGS. 1-7 demonstrate the various anchors, namely malar anchors 32, 132, 232, 332, and 432, cranial anchor 38, 138, 238, 338, and 438, and maxillary anchor 86, with a certain number of connection loops 90, namely four, four, and eight, respectively. One skilled in the art would realize that this number may be reduced or increased without affecting the operability of the malar anchors, cranial anchors, or maxillary anchor.

Alternative embodiments of the illustrated invention may incorporate malleable connection loops 90 on malar anchor 32, cranial anchor 38, and maxillary anchor 86. This would allow malar anchor 32, cranial anchor 38, and maxillary anchor 86 to sit flush against the respective bone surfaces even when the bone surface is uneven.

A further alternative embodiment of the illustrated invention may incorporate connection loops 90 of malar anchor 32, cranial anchor 38, and maxillary anchor 86 that are readily removable with standard tools. This allows simple and quick adjustment of malar anchor 32, cranial anchor 38, and maxillary anchor 86 to fit different sized patients or uneven mounting surfaces on a patient.

Figure 9:
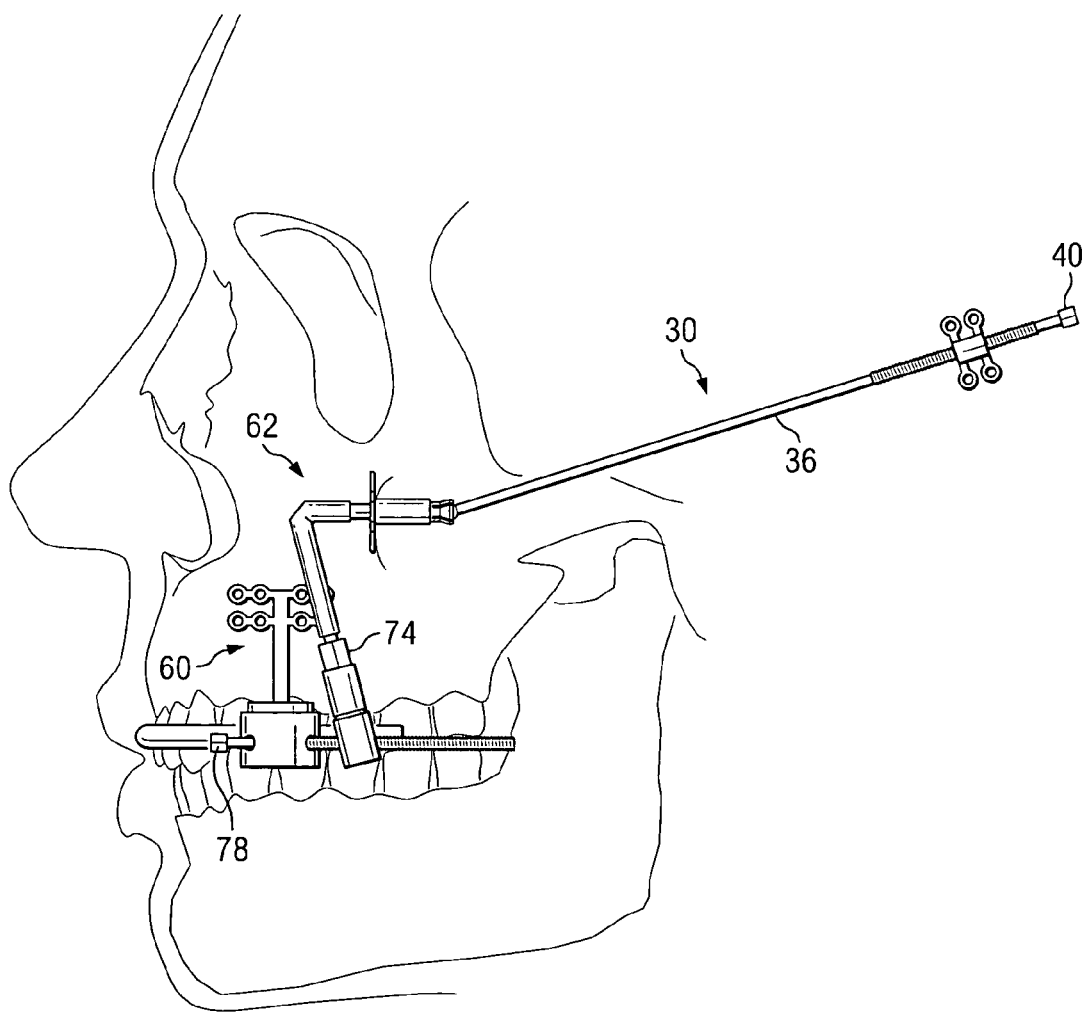
FIG. 9 is a side view of the implantable distraction unit of FIG. 8 as it may be implanted in a patient, in accordance with a particular embodiment of the present invention.
Figure 10:
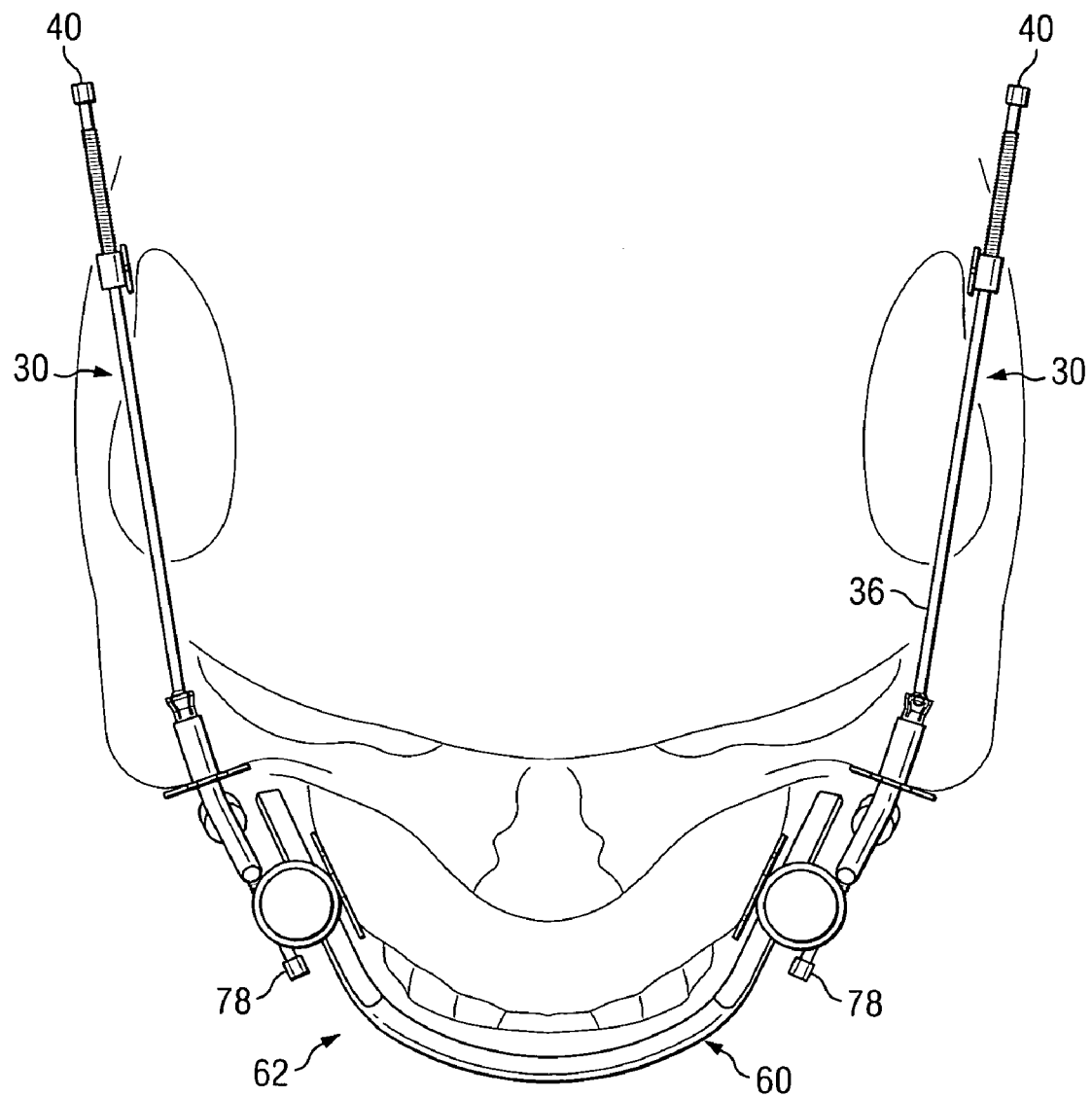
FIG. 10 is a top view of the implantable distraction unit of FIG. 8 as it may be implanted in a patient, in accordance with a particular embodiment of the present invention.

FIG. 9 and FIG. 10 illustrate implantable distraction unit 62 of FIG. 8 as it might be installed in a patient. FIG. 9 demonstrates a side view from the left side of the patients face with the overlaying tissue removed. FIG. 10 is a view from the top of a patient's head with the overlaying tissue removed. As the embodiment shown in FIG. 9 and FIG. 10 illustrates, most of implantable distraction unit 62 is internal to the patient. Hex nut 40 and a small section of distraction rod 36 are the only portions of implantable distraction unit 62 visible outside the body. Hex nut 40 is situated outside the scalp to allow for adjustment and/or removal of midface distraction device 30 without surgery. Placement of hex nut 40 in the hairline has the further effect of concealing any resulting scarring.

Most of maxillary spanner 60 is disposed within the patient's mouth between the upper dentition and top lip and cheeks. This placement of maxillary spanner 60 allows adjustment of horizontal distraction screw 74 and hex nut 78 without surgery. Placement of implantable distraction unit 62 internally, while preserving external adjustment capabilities, results in reduced patient scarring, trauma, and recovery time.

Although the present invention has been described in several embodiments, a myriad of changes and modifications may be suggested to one skilled in the art, and it is intended that the present invention encompass such changes and modifications as fall within the scope of the present appended claims.

What is claimed is:

1. A system for midface distraction, comprising:
a left side distraction mechanism and a right side distraction mechanism, each comprising:
a first implantable anchor configured to be coupled to a bone of the malar region ("the malar bone");
a second implantable anchor configured to be coupled to a bone of the cranium ("the cranial bone"); and
a distraction rod that, once coupled to the first implantable anchor and the second implantable anchor, comprises a free end disposed on a first side of the second implantable anchor and a moveable engagement disposed on an opposite side of the second implantable anchor wherein the moveable engagement comprises a ball-and-socket joint coupling the distraction rod to the first implantable anchor; and
a maxillary bridge configured to couple the left side distraction mechanism with the right side distraction mechanism, and wherein couplings between the maxillary bridge and the right and left distraction mechanisms are configured to be internal to a patient.

2. The system of claim 1, wherein:
the second implantable anchors include internally threaded housings operable to engage external threads on the distraction rods;
rotating the free ends imparts distractive force on the first and second implantable anchors once the distraction rods are threadably engaged with the second implantable anchors and coupled to the first implantable anchors; and
the distractive force pushes the first implantable anchors away from the second implantable anchors.

3. The system of claim 1, further comprising at least a third anchor configured to couple the maxillary bridge to the maxilla bone.

4. The system of claim 1, wherein the maxillary bridge is coupled to the right side distraction mechanism by a right side distraction arm, and the maxillary bridge is coupled to the left side distraction mechanism by a left side distraction arm, and wherein the right and left side distraction arms each comprise:
a substantially horizontal distraction screw configured to move the maxillary bridge substantially horizontally in relation to the right and left side distraction mechanisms; and
a substantially vertical distraction screw configured to move the maxillary bridge substantially vertically in relation to the right and left side distraction mechanisms.

5. The system of claim 1, wherein the maxillary bridge comprises a plurality of connection points configured to couple the maxillary bridge to an upper dentition.

6. The system of claim 1, wherein the distraction rod, once coupled between the first implantable anchor and the second implantable anchor, comprises a single rigid member directly connected to the first implantable anchor and the second implantable anchor.

7. The system of claim 1, wherein:
the first implantable anchor comprises one or more first connection loops that rigidly couple the first implantable anchor to the malar bone once one or more first bone screw are inserted into the malar bone through the one or more first connection loops; and
the second implantable anchor comprises one or more second connection loops that rigidly couple the second implantable anchor to the cranial bone once one or more second bone screws are inserted into the malar bone through the one or more second connection loops.

8. A system for midface distraction comprising:
a distraction rod;
a first implantable anchor being configured to be coupled to a bone of the malar region;
a second implantable anchor being configured to be coupled to a bone of the cranium; and wherein:
the distraction rod, once coupled to the first implantable anchor and the second implantable anchor, comprises a free end disposed on a first side of the second implantable anchor and a moveable engagement disposed on an opposite side of the second implantable anchor wherein the moveable engagement comprises a ball-and-socket joint coupling the distraction rod to the first implantable anchor.

9. A system for midface distraction, comprising:
a left side distraction mechanism and a right side distraction mechanism, each comprising:
a first implantable anchor configured to be coupled to a bone of the malar region, the first implantable anchor comprising a pin;
a second implantable anchor configured to be coupled to a bone of the cranium;
a distraction rod comprising a socket sized to capture the pin, wherein:
the distraction rod, once coupled to the first implantable anchor and the second implantable anchor, comprises a free end disposed on a first side of the second implantable anchor and a moveable engagement disposed on an opposite side of the second implantable anchor wherein the moveable engagement comprises a pin and socket joint coupling the distraction rod to the first implantable anchor; and
a maxillary bridge configured to couple the left side distraction mechanism with the right side distraction mechanism, and wherein couplings between the maxillary bridge and the right and left distraction mechanisms are configured to be internal to a patient.

10. The system of claim 9, wherein the pins are held in the sockets by forces imparted by the distraction rods.

11. A system for midface distraction comprising:

a left side distraction mechanism and a right side distraction mechanism, each comprising:

a distraction rod comprising a first end, a second end, and a threaded portion disposed between the first end and the second end;

a first implantable anchor;

a second implantable anchor comprising a internally threaded housing; wherein once the distraction rod is coupled to the first implantable anchor and the second implantable anchor:

the first end of the distraction rod moveably couples the distraction rod to the first implantable anchor;

the threaded portion of the distraction rod threadably couples the distraction rod to the second implantable anchor;

the second end comprises a free end disposed on an opposite side of the a second implantable anchor from the first end; and the distraction rod couples the first implantable anchor with the second implantable anchor; and a maxillary bridge configured to couple the left side distraction mechanism with the right side distraction mechanism, and wherein couplings between the maxillary bridge and the right and left distraction mechanisms are configured to be internal to a patient.

12. The system of claim 11, wherein the distraction rod includes:

a hollow tube;

flared flanges disposed on one end of the hollow tube; and a compression rod configured to pass through the hollow tube and engage the flared flanges.

13. The system of claim 11, wherein:

the first implantable anchor comprises a pin;

the distraction rod comprises a socket sized to capture the pin; and the socket moveably couples the distraction rod to the first implantable anchor once the pin is captured by the socket.

14. The system of claim 11, wherein rotating the free end imparts distractive force on the first and second implantable anchors to push the first implantable anchor away from the second implantable anchor.

15. The system of claim 11, the first implantable anchor is configured to reside between the malar bone and a layer of skin;

the second implantable anchor is configured to reside between the malar bone and a layer of skin; and the first end of the distraction rod is configured to reside on a first side of the layer of skin and the second end of the distraction rod resides on an opposite side of the layer of skin.

16. The system of claim 11, wherein the moveable couple allows for rotational movement of the distraction rod relative to the first and second implantable anchors during distraction.

17. The system of claim 11, wherein the moveable coupling allows for pivotal movement of the distraction rod relative to the first implantable anchor.

* * * * *

UNITED STATES PATENT AND TRADEMARK OFFICE
CERTIFICATE OF CORRECTION

PATENT NO.       : 7,621,922 B2            Page 1 of 1
APPLICATION NO.  : 10/924315
DATED            : November 24, 2009
INVENTOR(S)      : Schendel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1324 days.

Signed and Sealed this

Twenty-sixth Day of October, 2010

David J. Kappos
*Director of the United States Patent and Trademark Office*